United States Patent [19]

Sturm

[11] 4,264,604
[45] Apr. 28, 1981

[54] QUINOLONECARBOXYLIC ACID DERIVATIVES AS BACTERICIDES

[75] Inventor: Elmar Sturm, Aesch, Switzerland

[73] Assignee: Ciba-Geigy Corporation, Ardsley, N.Y.

[21] Appl. No.: 918,999

[22] Filed: Jun. 26, 1978

[30] Foreign Application Priority Data

Jul. 1, 1977 [CH] Switzerland .................. 8130/77
Jun. 8, 1978 [CH] Switzerland .................. 6285/78

[51] Int. Cl.³ .................. A01N 43/42; C07D 215/56
[52] U.S. Cl. .................................. 424/258; 546/156
[58] Field of Search .............. 260/287 AN; 424/258; 546/156

[56] References Cited

U.S. PATENT DOCUMENTS

| B 344,479 | 1/1975 | Gerster | 424/258 |
| 3,849,421 | 11/1974 | Nakagome et al. | 260/287 AN |
| 3,924,042 | 12/1975 | Gerster | 424/258 |
| 4,146,625 | 3/1979 | Lee | 424/258 |

FOREIGN PATENT DOCUMENTS 863429 1/1978 Belgium .
2407744 8/1974 Fed. Rep. of Germany .
830832 1/1958 United Kingdom .

Primary Examiner—Donald G. Daus
Assistant Examiner—Diana G. Rivers
Attorney, Agent, or Firm—Frederick H. Rabin

[57] ABSTRACT

Phytobactericidal compositions which contain, as active ingredient, a compound of the formula I, or one of the salts thereof,

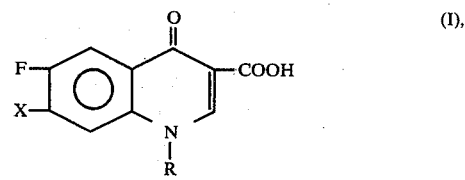

wherein X represents hydrogen, fluorine or chlorine, and R represents a lower alkyl group, are suitable for combating Erwinia spp., particularly *E. amylovora* (fireblight on fruit trees) and *E. carotovora* (soft rot on potatoes and vegetables).

4 Claims, No Drawings

QUINOLONECARBOXYLIC ACID DERIVATIVES AS BACTERICIDES

The present invention relates to bactericidal compositions and to a process for combating species of Erwinia by application of a compound of the formula I

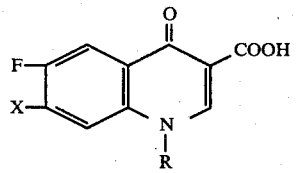

wherein X represents hydrogen, fluorine or chlorine, and R represents a lower alkyl group, or by application of salts thereof.

By lower alkyl groups within the scope of this invention are meant methyl, ethyl, propyl, isopropyl, butyl, isobutyl, and sec-butyl.

And by salts are meant salts of strong organic bases, such as methylamine and triethylamine, particularly however salts of inorganic alkali metals and alkaline-earth metals and also ammonia.

Among the species of Erwinia there are some that give rise to serious bacterioses which are economically very disadvantageous. There are on the one hand the pathogens of soft rot of plants, for example *E. carotovora*, *E. atroseptica* and *E. chrysanthemi;* and on the other hand the pathogens of fireblight, *E. amylovora*. In the first group, named after the main pathogen, *E. carotovora*, are comprised all species of the dreaded soft rot, which can cause after harvesting in the case of many varieties of vegetables, beet and potatoes, catastrophic damage under unfavourable storage conditions (high humidity and shortage of oxygen owing to poor ventilation). In the field too, however, pathogens of the *E. carotovora* group are capable of destroying the seed, for example potato tubers, even before germination (see piece decay). Potato plants can show the symptoms of black leg; and beet, cabbage and konnyaku can be damaged in a simlar manner.

In order to combat these bacteria, there are carried out in some cases immersion treatments with sodium hypochlorite (NaOCl), or spraying applications with streptomycin, but none of these measures has been sufficiently successful.

Compared however with these applied substances, the small group of halogenated quinolonecarboxylic acids of the formula I has proved extraordinarily effective. Preferred compounds among these are above all those of the formula I and salts thereof wherein X represents hydrogen or chlorine, and R represents a lower alkyl group, preferably ethyl, propyl and isopropyl.

Fireblight, caused by the bacteria Erwinia amylovora, is one of the most feared and economically most serious diseases affecting pomaceous fruit. This bacteriosis was first observed on the east coast of the U.S.A.; it then traversed in one single sweep the North American continent, and produced at the beginning of the twentieth century in California, Oregon and Washington a devastating epidemic in the apple and pear crops existing there. In consequence of fireblight, the commercial cultivation of pears in the U.S.A. today is limited mainly to the arid regions of California. In the year 1957, fireblight was verified in England, and 10 years later isolated centres of this disease were observed also on the European continent. In spite of vast land clearing undertakings, with which an attempt was made to wipe out these centres of infestation, fireblight was able to spread and to become firmly established in Northern Europe (Denmark, Schleswig Holstein, Holland, and regions of France and Belgium). For the time being in the European regions concerned it is particularly shrubs of the Rosaceae family (Crataegus, Cotoneaster, etc.) which are infested, but it is not to be doubted that there will be a further penetration of the disease also into the vast fruit-cultivation areas. The continual advance of this disease proves the inadequacy of the measures taken hitherto (use of streptomycin, copper preparations, etc.).

It has now been found that, surprisingly, the small group of quinolonecarboxylic acids of the formula I can protectively prevent in particular fireblight.

Quinolonecarboxylic acids have been suggested in a general form as therapeutics in the British Patent Specification No. 830,832. A phytobactericidal action is however not mentioned. A predominant part of the compounds mentioned therein are completely ineffectual against E. amylovora.

The compounds of the formula I are produced by reaction at 20°–160° C. of an aniline derivative of the formula II with an alkoxymethylenemalonic acid ester with the splitting-off of alkanol; cyclisation of the resulting anilinomethylenemalonic acid ester of the formula III at elevated temperature of 200°–280° C.; splitting-off of the alkoholic part of one of the ester groups to give the 4-hydroxyquinoline-3-carboxylic acid ester of the formula IV; and subsequent introduction of a substituent R by means of customary alkylation with, e.g., an alkyl halide (such as alkyl bromide or alkyl iodide). The quinolonecarboxylic acid ester of the formula V obtained can be saponified with bases to give compounds of the formula I and is then in the salt form, from which it can be converted, if required, by acidification into the free carboxylic acid:

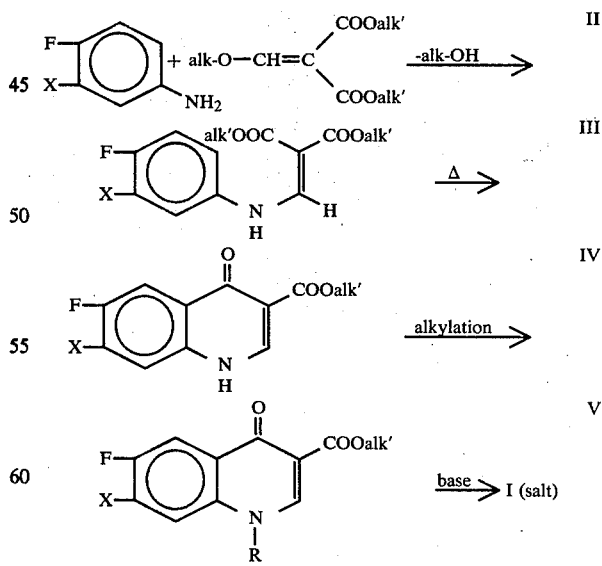

(alk and alk' are any desired alkyl groups that can be split off)

The quinolonecarboxylic acids of the formula I are stable compounds insoluble in most organic solvents at normal temperature, and partially soluble in water, readily soluble however on the addition of alkalies or strong amines. By acidification, with e.g., mineral acids, they can be precipitated, or stabilised as colloidal solutions.

A compound to be particularly emphasised by virtue of its action is the compound No. 2 described in the following Example; others to be emphasised are the subsequent compounds Nos. 1 and 14.

The invention relates also to the new compounds of the formula I wherein X represents fluorine or chlorine, and R represents a lower alkyl group, or wherein X represents hydrogen, and R represents methyl, propyl, isopropyl, butyl, isobutyl and sec-butyl.

Production of 1-ethyl-7-chloro-6-fluoro-4-quinolone-3-carboxylic acid

1st Stage: 21.8 g of 3-chloro-4-fluoroaniline is mixed with 32.4 g of ethoxymethylenemalonic acid diethyl ester, and the mixture is heated for 30 minutes at 150° C., with alcohol distilling off. The melt solidifies after cooling to form a crystal mass. There is thus obtained 47 g of crude 3-chloro-4-fluoroanilinomethylenemalonic acid diethyl ester, m.p. 67°–70° C.

2nd Stage: 35.5 g of the preceding compound is heated in 300 ml of DOWTHERM A for 1 hour at 240°–250° C., in the course of which alcohol distills off. After cooling, the mixture is stirred up with the double volume of petroleum ether, and the crystal sludge is filtered off with suction to yield 20 g of 7-chloro-6-fluoro-4-hydroxyquinoline-3-carboxylic acid ethyl ester, m.p. 283°–290° C.

3rd Stage: 20 g of the preceding compound is suspended in 200 ml of dimethylformamide, and 3.9 g of a 50% sodium hydride dispersion is added. After the evolution of hydrogen has ceased, the reaction mixture is heated for 1 hour at 80° C., and 17 g of ethyl iodide is added. Stirring is maintained, at 80°–90° C. internal temperature, under reflux for 5 hours until a clear solution has formed. The dimethylformamide is to a great extent removed in vacuo; 200 ml of water and 10 g of sodium hydroxide are added, and the mixture is stirred under reflux for 2 hours. Some animal charcoal is added to the alkaline solution; the solution is then filtered and rendered acid with conc. hydrochloric acid. The precipitate which has separated out is filtered off with suction, and whilst still moist recrystallised from dimethylformamide to thus yield 15 g of the title compound as colourless crystals, m.p. 279°–281° C.

The following compounds are produced in the manner described or in a similar manner:

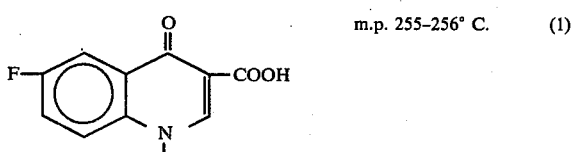  m.p. 255–256° C.  (1)

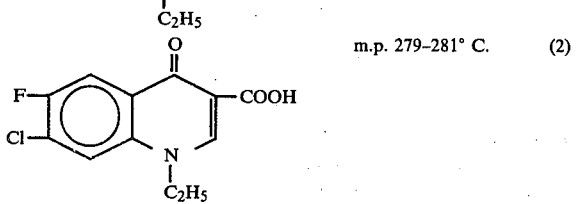  m.p. 279–281° C.  (2)

-continued

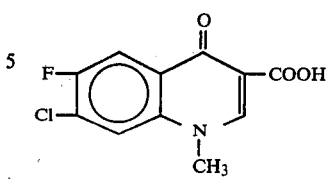  m.p. > 300° C.  (3)

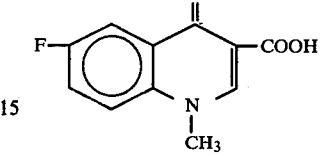  m.p. 298–299° C.  (4)

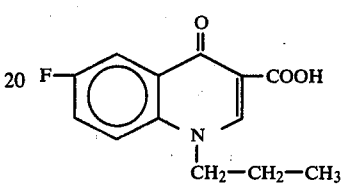  m.p. 235–238° C.  (5)

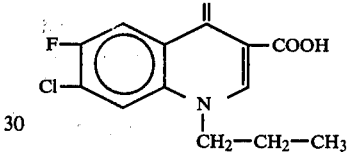  m.p. 220–240° C.  (6)

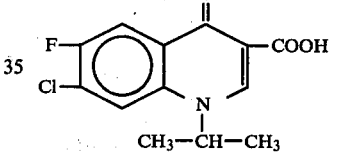  m.p. 205–212° C.  (7)

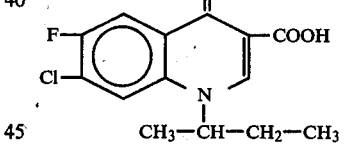  m.p. 208–215° C.  (8)

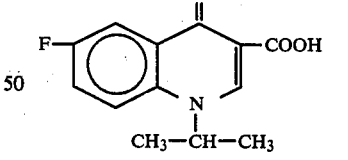  m.p. 200–205° C.  (9)

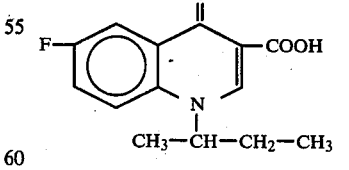  m.p. 207–212° C.  (10)

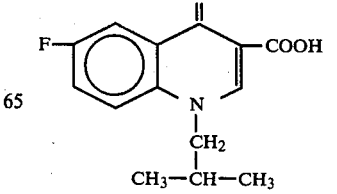  m.p. 194–198° C.  (11)

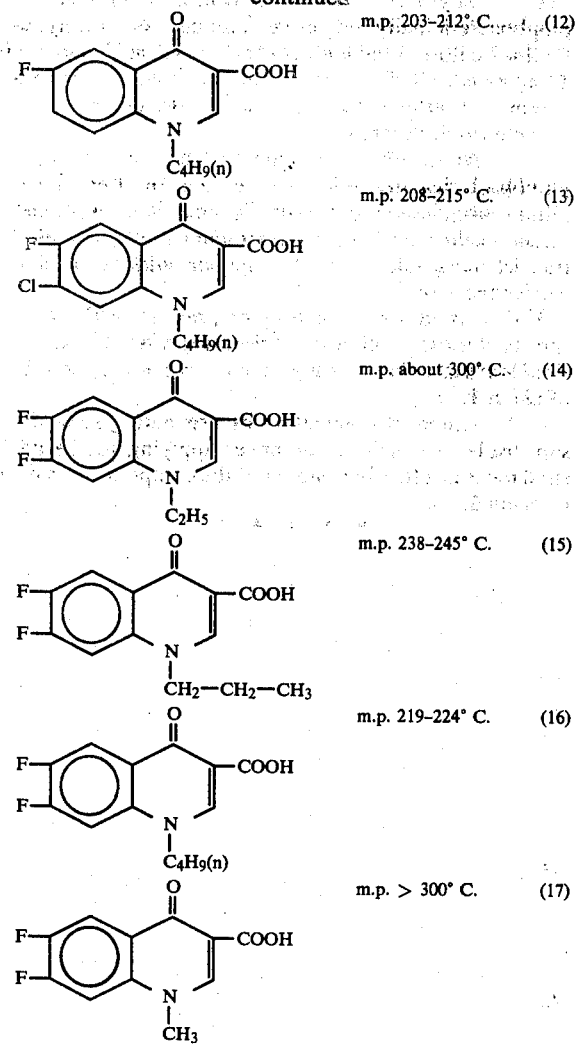

-continued m.p. 203-212° C. (12)

m.p. 208-215° C. (13)

m.p. about 300° C. (14)

m.p. 238-245° C. (15)

m.p. 219-224° C. (16)

m.p. > 300° C. (17)

The compounds of the formula I can be used on their own or together with suitable carries and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commercial compositions is between 0.1 and 90%.

For application, the compounds of the formula I can be in the following forms (the weight-percentage figures in brackets signify advantageous amounts of active substance):

solid preparations: dusts and scattering agents (up to 10%), granulates [coated granules, impregnated granules and homogeneous granules] and pellets 1 to 80%);

liquid preparations:

(a) water-dispersible concentrates of active substance:
 wettable powders and pastes (25 to 90% in the commercial packing, 0.01 to 15% in ready-for-use solutions);
 emulsion concentrates and solution concentrates 10 to 50%, 0.01 to 15% in ready-for-use solutions);

(b) solutions (0.1 to 20%); aerosols.

The active substances of the formula I of the present invention can be formulated for example as follows:

Wettable Powder

The following constituents are used to product (a) a 40% wettable powder and (b) a 10% wettable powder;

(a)

40 parts of active substance,
5 parts of sodium lignin sulphonate,
1 part of sodium dibutyl-naphthalene sulphonate, and
54 parts of silicic acid;

(b)

10 parts of active substance,
3 parts of a mixture of the sodium salts of saturated fatty alcohols sulphates,
5 parts of naphthalenesulphonic acid/formaldehyde condensate, and
82 parts of kaolin.

The active substances are intimately mixed, in suitable mixers, with the additives, and the mixture is ground in the appropriate mills and rollers. There are obtained wettable powders which have excellent wettings and suspension properties, which can be diluted with water to give suspensions of the concentration desired, and which can be used in particular for leaf application.

Emulsifiable Concentrate

The following substances are used to produce a 25% emulsifiable concentrate:

25 parts of active substance,
2.5 parts of epoxidised vegetable oil,
10 parts of an alkylarylsulphonate/fatty alcohol polyglycol ether mixture,
5 parts of dimethylformamide, and
57.5 parts of xylene.

From such concentrates it is possible to prepare, by dilution with water, emulsions of the desired concentration, which are particularly suitable for leaf application.

BIOLOGICAL EXAMPLE 1

The test substances, formulated as wettable powders, are suspended in water, and the suspensions obtained are sprayed at different concentrations (1000 to 100 ppm of active substance) onto one-year-old pear seedlings of the Bartlett variety until these are dripping wet. Infection of the young trees is effected 24 hours later by spraying them with an aqueous suspension of a virulent strain of *Erwinia amylovora.* Immediately after infection, the plants are placed for 24 hours into an air-conditioned chamber at 25° C. with 100% relative humidity, and there is subsequently performed further incubation in a conventional greenhouse. Seven days after infection, the test is evaluated by determining the percentage of diseased plants per treatment. Twenty young trees are used for each treatment. Streptomycin is used as a standard, and as control specimens are used young trees which have been treated only with water before being infected.

In contrast to the infection of the untreated plants and to that of the plants treated with streptomycin, the disease development in the case of the young trees treated with compounds Nos. 1, 3 and 17 was prevented almost completely. Young trees which had been treated with suspensions of the compound No. 2 or of the compound No. 14 showed no disease symptoms of *E. amylovora* at all.

BIOLOGICAL EXAMPLE 2

Potato tubes are cut into two. The halves are immersed for 5 minutes in aqueous suspensions containing 40 ppm and 10 ppm of active substance, respectively, and are then allowed to superficially dry on glass dishes. After 2 hours they are sprayed with a bacterial suspension of *Erwinia carotovora*. Halves of tubers which have not been immersed are simultaneously infected and serve as control specimens. All infected tubes are subsequently incubated at about 26° C. with 90–100% relative humidity. Four days after infection, the untreated tubers have decomposed into the form of pulp; the action of the active substance on the treated tubers can therefore be visually assessed.

The compounds of the formula I exhibited consistently with 40 ppm of active substance a complete protective action. In addition to other compounds, the compound No. 2 in particular showed this action, even at a concentration of 10 ppm.

I claim:

1. A phytobactericial composition comprising a phytobactericidally effective amount of 1-ethyl-6-fluoro-7-chloro-4-quinolone-3-carboxylic acid and the alkali metal, alkaline earth metal, ammonium, methylamine or triethylamine salts thereof, together with a suitable carrier therefor.

2. A phytobactericidal composition comprising a phytobactericidally effective amount of 1-ethyl-6,7-difluoro-4-quinolone-3-carboxylic acid and the alkali metal, alkaline earth metal, ammonium, methylamine or triethylamine salts thereof, together with a suitable carrier therefor.

3. A method for combatting or preventing Erwinia-spp. bacterioses which comprises applying to the desired locus an effective amount of the compound or salts of claim 1.

4. A method of combatting or preventing Erwinia-spp. bacterioses which comprises applying to the desired locus an effective amount of the compound or salts of claim 2.

* * * * *